(12) United States Patent
Kim et al.

(10) Patent No.: US 10,427,085 B2
(45) Date of Patent: Oct. 1, 2019

(54) CLEANING ROBOT

(71) Applicant: Samsung Electronics Co., Ltd., Suwon-si (KR)

(72) Inventors: Byung Chan Kim, Yongin-si (KR); Woo Ram Oh, Suwon-si (KR); Sang Sik Yoon, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 874 days.

(21) Appl. No.: 14/882,195

(22) Filed: Oct. 13, 2015

(65) Prior Publication Data
US 2016/0100733 A1   Apr. 14, 2016

(30) Foreign Application Priority Data
Oct. 13, 2014 (KR) .......... 10-2014-0137405

(51) Int. Cl.
 *B01D 50/00* (2006.01)
 *A47L 9/16* (2006.01)
 *A61L 9/00* (2006.01)
 *A47L 9/28* (2006.01)

(52) U.S. Cl.
 CPC .......... *B01D 50/002* (2013.01); *A47L 9/1666* (2013.01); *A47L 9/1683* (2013.01); *A47L 9/2805* (2013.01); *A61L 9/00* (2013.01); *A47L 2201/022* (2013.01); *F24F 2221/42* (2013.01)

(58) Field of Classification Search
 CPC .......... A47L 2201/00–06; A47L 9/281; A47L 9/2805; A47L 9/1666; A47L 9/1683; A47L 2201/022; A61L 9/00–22; B01D 50/002; F24F 2221/42

USPC .................................................. 15/319, 339
See application file for complete search history.

(56) References Cited

U.S. PATENT DOCUMENTS

| | | | |
|---|---|---|---|
| 2005/0166355 A1* | 8/2005 | Tani ...................... | A47L 9/2805 15/319 |
| 2005/0171644 A1* | 8/2005 | Tani ....................... | A47L 9/009 700/253 |
| 2007/0050937 A1* | 3/2007 | Song ...................... | A47L 5/225 15/319 |
| 2008/0056933 A1* | 3/2008 | Moore .................... | A47L 11/30 422/1 |

(Continued)

FOREIGN PATENT DOCUMENTS

| | | | |
|---|---|---|---|
| CN | 101306283 | * 11/2008 | ............. B01D 46/00 |
| JP | 2005331128 | 12/2005 | |
| KR | 20070099275 | 10/2007 | |

(Continued)

*Primary Examiner* — David Redding
(74) *Attorney, Agent, or Firm* — Staas & Halsey LLP

(57) ABSTRACT

Disclosed herein is a cleaning robot including a body; a display unit configured to display information related to various operations of the cleaning robot; a dust collecting box separably coupled with the body to collect dust introduced through a dust suction port; an air cleaning box to replace the dust collecting box and installed at the body to purify air introduced into the body and then discharge the purified air; and a control unit configured to recognize whether a box installed at the body is the dust collecting box or the air cleaning box, and to control the cleaning robot to perform a cleaning mode or an air cleaning mode according to a recognized result.

16 Claims, 24 Drawing Sheets

(56) References Cited

U.S. PATENT DOCUMENTS

2008/0206092 A1* 8/2008 Crapser .................. A47L 11/24
             422/5
2018/0225943 A1* 8/2018 Meyer .................. G08B 17/103

FOREIGN PATENT DOCUMENTS

| KR | 20060112376 | 3/2008 |
| KR | 20090030119 | 3/2009 |
| KR | 20120090413 | 8/2012 |

* cited by examiner

CLEANING ROBOT

RELATED APPLICATION(S)

This application claims the benefit of Korean Patent Application No. 10-2014-0137405, filed on Oct. 13, 2014 in the Korean Intellectual Property Office, the disclosure of which is incorporated herein by reference.

BACKGROUND

Embodiments of the present invention relate to a cleaning robot.

A cleaning robot is an apparatus which removes foreign substances such as dust, while traveling automatically over an area to be cleaned without a user's operation, and performs a cleaning operation while traveling along a predetermined traveling pattern. Also, the cleaning robot may determine a distance to an obstacle installed within a cleaning area, such as furniture, a wall and a home appliance, through a sensor, and may change a direction automatically by selectively driving a left motor and a right motor.

In such a cleaning robot, suctioned dust is collected in a dust collecting part, and an alarm is generated to remove the dust in the dust collecting part, when a predetermined amount of the dust is accumulated in the dust collecting part.

Meanwhile, to perform an automatic cleaning operation without a user's help, the cleaning robot may include not only a sensor part and a driving unit, but also a high-performance central processing unit (CPU) part having a fast processing speed and a high-powered motor for a high-efficiency cleaning operation.

Currently, the above-described specification is simply used for only a purpose of cleaning a floor.

SUMMARY

Therefore, it is an aspect of the present invention to provide a cleaning robot capable of providing various services to a user based on the above-described performance.

Additional aspects of the invention will be set forth in part in the description which follows and, in part, will be obvious from the description, or may be learned by practice of the invention.

In accordance with one aspect of the present invention, a cleaning robot includes a display unit configured to display information related to operations of the cleaning robot; a dust suction port; a body to removably receive at least one of a dust collecting box and an air cleaning box, wherein the dust collecting box is separably coupled with the body and collects dust introduced through the dust suction port, and wherein the air cleaning box purifies air introduced into the body and discharges the purified air; and a control unit to recognize whether a box installed at the body is the dust collecting box or the air cleaning box, and to control the cleaning robot to perform a cleaning mode or an air cleaning mode according to a recognized result.

The air cleaning box may include a filter to filter the dust and odor particles from the air introduced into the body.

The air cleaning box may include a contamination detecting sensor located at a passage, through which the air is introduced into or discharged from the body, to detect a contamination level of the air introduced into the body.

Each of the dust collecting box and the air cleaning box has a contact type connector for at least one of a power supply and a signal transmission provided at an area coupled to the body, and is coupled to the body via the contact type connector.

The dust collecting box may have a dust introduction hole formed at a position connected with a passage through which the dust introduced through the dust suction port is transferred.

The control unit may recognize a replacement of at least one of the dust collecting box and the air cleaning box through replacement information input by a user.

Each of the dust collecting box and the air cleaning box has a switch recognizing part enabling the control unit to recognize which of the dust collecting box and the air cleaning box has been installed.

The control unit may recognize one of the dust collecting box and the air cleaning box through one of a first switch for recognizing the air cleaning box and a second switch for recognizing the dust collecting box provided at the body, contacting with the switch recognizing part.

Each of the dust collecting box and the air cleaning box has a magnet enabling the control unit to recognize which of the dust collecting box and the air cleaning box has been installed.

The control unit may recognize one of the dust collecting box and the air cleaning box through one of a first hole sensor for recognizing the air cleaning box and a second hole sensor for recognizing the dust collecting box provided at the body, through the magnet.

The cleaning robot may further include a suction motor to generate a suction force to collect dust dispersed in the dust collecting box through the dust suction port, wherein the control unit detects a load applied to the suction motor enabling the control unit to recognize which of the dust collecting box and the air cleaning box has been installed based on the load.

The control unit may recognize which of the dust collecting box and the air cleaning box has been installed based on an output data signal of a contamination detecting sensor located in the air cleaning box.

The control unit may recognize which of the dust collecting box and the air cleaning box has been installed, and automatically switches to one of the dust collecting mode and air cleaning mode.

In the air cleaning mode, the control unit may control the body to perform an air cleaning operation while moving in a predetermined air cleanable area unit.

In the air cleaning mode, the control unit may control the body to perform an air cleaning operation based on position and time information set by a user.

In the air cleaning mode, when contamination is detected while the body is traveling, the control unit controls the body to perform an air cleaning operation until a contamination level within an area becomes lower than or equal to a predetermined reference value.

The control unit may control the body to perform an air cleaning operation while moving in a contaminated area of a contamination map.

When a battery residual value of the cleaning robot is less than or equal to a reference value, or an air cleaning operation is completed, the control unit may control the body to return to a charging station.

The control unit may control controls the cleaning robot to purify the air, while being charged at a charging station.

When a contamination level detected by a contamination detecting sensor is greater than or equal to a reference value for more than a predetermined period of time, the control unit may determine an error of the contamination detecting sensor, and controls the cleaning robot to perform an air cleaning operation with a predetermined suction force.

When a contamination level detected by a contamination detecting sensor is greater than or equal to a reference value for more than a predetermined period of time, the control unit may display an air contamination alarm of a corresponding area through the display unit, output the air contamination alarm as a sound source through an audio output unit, or transfer the air contamination alarm to a user's mobile communication terminal through wireless communication.

BRIEF DESCRIPTION OF THE DRAWINGS

These and/or other aspects of the invention will become apparent and more readily appreciated from the following description of the embodiments, taken in conjunction with the accompanying drawings of which.

DETAILED DESCRIPTION

Figure 1:
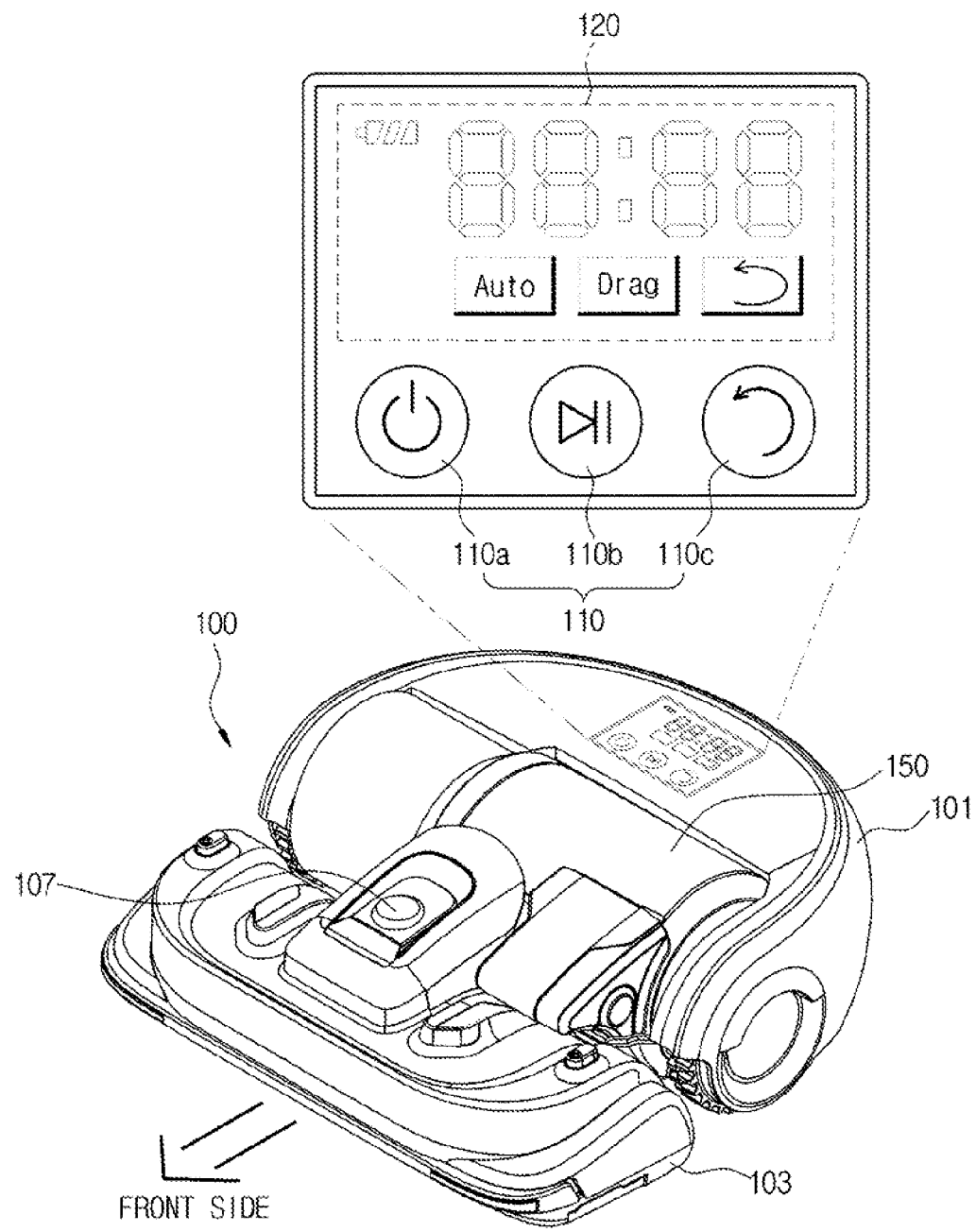
FIG. 1 is a view illustrating an exterior of a cleaning robot.

Objects, particular advantages and novel characteristics of the present invention will be more apparent from the following detailed description and preferred embodiments in connection with the accompanying drawings. In the drawings, the same components are designated by the same reference numerals, even though they are depicted in different drawings. In the following description, if it is considered that the specific description of the related and well known functions or structures may obscure the gist of the present invention, the specific description will be omitted. Furthermore, the terms "first," "second" and the like in the description and in the claims are used for distinguishing one component from other components, and thus the components should not be limited by the terms.

Hereinafter, exemplary embodiments of the present invention will be described in detail with reference to the accompanying drawings.

Figure 2:
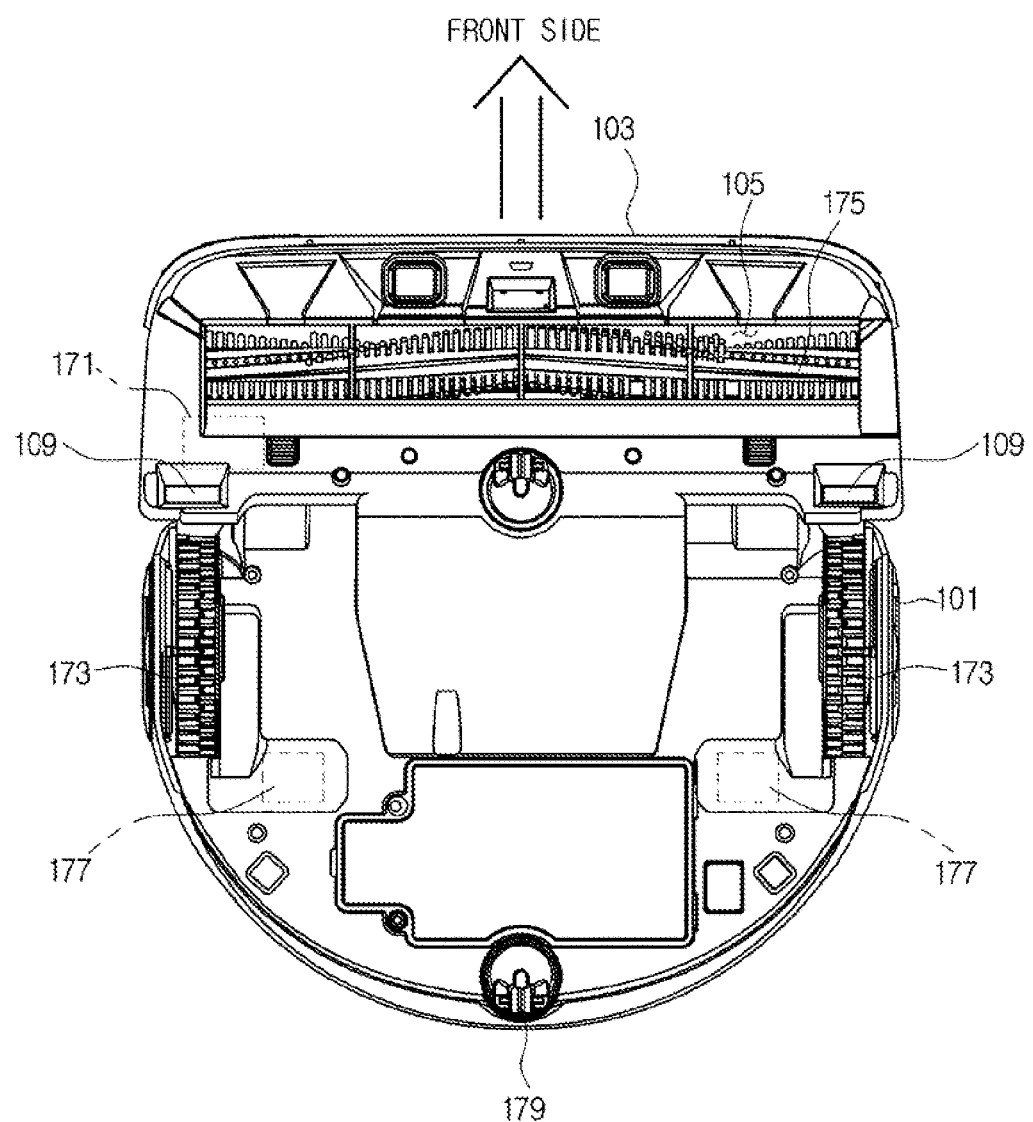
FIG. 2 is a bottom view of the cleaning robot of FIG. 1.

FIG. 1 is a view illustrating an exterior of a cleaning robot, and FIG. 2 is a bottom view of the cleaning robot.

Referring to FIGS. 1 and 2, the cleaning robot 100 may include a body including a main body 101 and a sub-body 103, a camera module 107, a step detecting module 109, an input unit 110, a display unit 120, a brush driving motor 171, a drum brush 175, traveling wheels 173 and a wheel driving motor 177.

The body may not be divided into the main body 101 and the sub-body 103, but may be integrally formed. Also, hereinafter, a reference numeral of the body will be designated by 101 or 103 for convenience of explanation.

As illustrated in FIG. 1, the main body 101 may have an approximate semi-cylindrical shape, and the sub-body 103 may have a rectangular parallelepiped shape, but the main body 101 and the sub-body 103 are not limited thereto.

Also, components for realizing a function of the cleaning robot 100 may be provided inside and outside of the main body 101 and the sub-body 103.

The camera module 107 may obtain an image around the cleaning robot 100, and may be disposed at an upper surface of the sub-body 103 to obtain an image of an upper side of the cleaning robot 100.

Also, the camera module 107 may include a lens that focuses on a light emitted from an upper side of the cleaning robot 100, and an image sensor that converts the light into an electric signal. At this time, the image sensor may be a complementary metal oxide semiconductor (CMOS) sensor or a charge coupled device (CCD) sensor.

Also, the camera module 107 may convert the image of the upper side of the cleaning robot 100 into the electric signal to be processed by a control unit 190, and may transfer the electric signal corresponding to the image of the upper side of the cleaning robot 100 to the control unit 190. At this time, the control unit 190 may use the transferred image of the upper side of the cleaning robot 100 to detect a position of the cleaning robot 100 and to generate map information of a cleaning area.

The step detecting module 109 may be formed at a bottom surface of the sub-body 103 to emit infrared light or ultrasonic waves toward a floor surface of the cleaning area and to detect the infrared light or the ultrasonic waves reflected from the floor surface of the cleaning area.

Specifically, the step detecting module 109 may transfer an intensity of the infrared light (or ultrasonic waves) reflected from the floor surface of the cleaning area, or a time interval between emission and detection of the infrared light (or ultrasonic waves) to the control unit 190.

The control unit 190 may determine the presence or absence of a step based on the intensity of the infrared light (or ultrasonic waves) reflected from the floor surface of the cleaning area, or the time interval between emission and detection of the infrared light (or ultrasonic waves). For example, when the intensity of the infrared light (or ultrasonic waves) reflected from the floor surface of the cleaning area is less than or equal to a predetermined reference intensity, it is determined that there may be a step, and when the time interval for transmitting the infrared light (or ultrasonic waves) reflected from the floor surface of the cleaning area is more than or equal to a predetermined reference time interval, it is determined that there may be a step.

The input unit 110 may be formed on an exterior surface of the cleaning robot 100 to receive an input of various control commands from a user.

The input unit 110 may include a power button 110a which turns on or off the cleaning robot 100, a start/stop button 110b which starts or stops operating of the cleaning robot 100, and a return button 110c which returns the cleaning robot 100 to a charging station (not shown). At this time, each input button 110a, 110b, 110c may be a push switch type button or membrane type button that generates an input signal through a pressing operation by the user, or a touch switching type that generates an input signal through touching by a part of a user's body.

The display unit 120 may display information related to various operations of the cleaning robot 100.

Also, the display unit 120 may display information of the cleaning robot 100 corresponding to the control commands input by the user. For example, the display unit 120 may display an operational state of the cleaning robot 100, a power state, a cleaning or dust collecting mode or an air cleaning mode, whether to return to the charging station, and the like.

Also, the display unit 120 may include self-luminous light emitting diodes (LEDs) or organic light emitting diodes (OLEDs), or a liquid crystal display having a separate light source.

The brush driving motor 171 is provided adjacent to the drum brush 175 to rotate the drum brush 175 according to a cleaning control signal of the control unit 190.

As illustrated in FIG. 2, the drum brush 175 is provided at a dust suction port 105, which is formed at the bottom surface of the sub-body 103, to disperse and/or collect dust on the floor adjacent the cleaning robot 100 into the dust suction port 105, while rotating about a rotating shaft (not shown) of the sub-body 103 provided in parallel with the cleaning floor.

The traveling wheels 173 may be provided at either ends of the bottom surface of the main body 10, and may include a left traveling wheel at a left side of the cleaning robot 100 with respect to a front side of the cleaning robot 100, and a right traveling wheel at a right side of the cleaning robot 100.

Also, the traveling wheel 173 may receive a rotational force from the wheel driving motor 177, and may move the cleaning robot 100.

The wheel driving motor 177 generates the rotational force for rotating the traveling wheels 173, and may include a left driving motor 177 which rotates the left traveling wheel 173, and a right driving motor 177 which rotates the right traveling wheel 173.

Each of the left driving motor 177 and the right driving motor 177 may receive a driving control signal from the control unit 190 to independently operate, drive, and rotate the left traveling wheel 173 and the right traveling wheel 173, respectively.

Also, since the left traveling wheel 173 and the right traveling wheel 173 may be independently rotated, the cleaning robot 100 may perform various traveling operations such as a forward movement, a backward movement, a turning movement and a spinning motion.

For example, when both of the left and right traveling wheels 173 are rotated in a first direction at similar or same speeds, the cleaning robot 100 may travel straight ahead (or may perform the forward movement), and when both of the left and right traveling wheels 173 are rotated in a second direction at similar or same speeds, the cleaning robot 100 may travel straight back (or may perform the backward movement).

Also, when both of the left and right traveling wheels 173 are rotated in the same direction but at different speeds, the cleaning robot 100 may turn to the right or left, and when both of the left and right traveling wheels 173 are rotated in different directions, the cleaning robot 100 may be spun about the same place in a clockwise or counterclockwise direction.

A caster wheel 179 may be installed at the bottom surface of the main body 101, and a rotating shaft (not shown) of the caster wheel 179 may be rotated according to a moving direction of the cleaning robot 100. The caster wheel 179 does not obstruct the movement of the cleaning robot 100, and allows the cleaning robot 100 to travel in a stable posture.

In addition, a driving unit 170 which will be described below may include a gear module (not shown) which reduces the rotational force of the wheel driving motor 177 and transmits the reduced rotational force to the traveling wheels 173, and a rotation detecting sensor (not shown) which detects a rotational displacement and a rotational speed of the wheel driving motor 177 or the traveling wheels 173.

Figure 3:
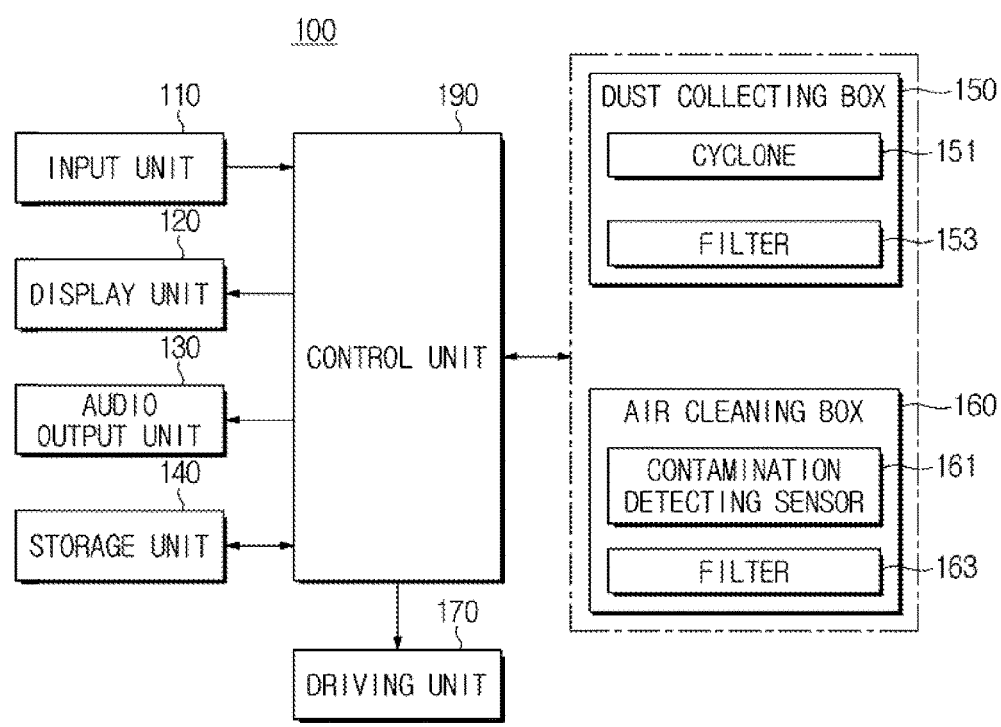
FIG. 3 is a block diagram illustrating a control structure of the cleaning robot of FIG. 1.

Meanwhile, referring to FIGS. 1 and 3, the cleaning robot 100 may include a dust collecting box 150 including a cyclone 151 and a filter 153.

The cyclone 151 may be provided at an inside of the main body 101, and may separate the dust and air introduced through the dust suction port 105, and may transfer the separated dust and air to the filter 153. More specifically, the cyclone 151 may be provided at an interior of the dust collecting box 150 in the main body 101, but the present invention is not limited thereto.

The cyclone 151 separates the dust and the air introduced through the dust suction port 105 and transferred via a guide tube (not shown), and then transfers only the air toward the filter 153. At this time, the air transferred toward the filter 153 may be discharged from the cleaning robot 100. That is, the cyclone 151 primarily separates the dust from the air before the air passes through the filter 153.

The filter 153 may filter out the dust separated by the cyclone 151 and other dust contained in the air, and thus may allow only the air to be discharged from the cleaning robot 100.

Although not shown in the drawings, the cleaning robot 100 may further include a suction motor to generate a suction force to collect the dust introduced through the dust suction port 105 in the dust collecting box 150, and a suction fan rotated by the suction motor to generate the suction force to collect the dust into the dust collecting box 150.

Figure 4:
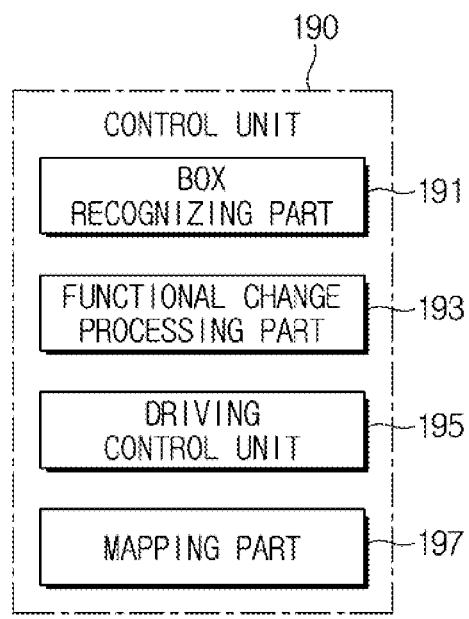
FIG. 4 is a block diagram illustrating a structure of a control unit of FIG. 3.

FIG. 3 is a block diagram illustrating a control structure of the cleaning robot, and FIG. 4 is a block diagram illustrating a structure of a control unit of FIG. 3.

Figure 5:
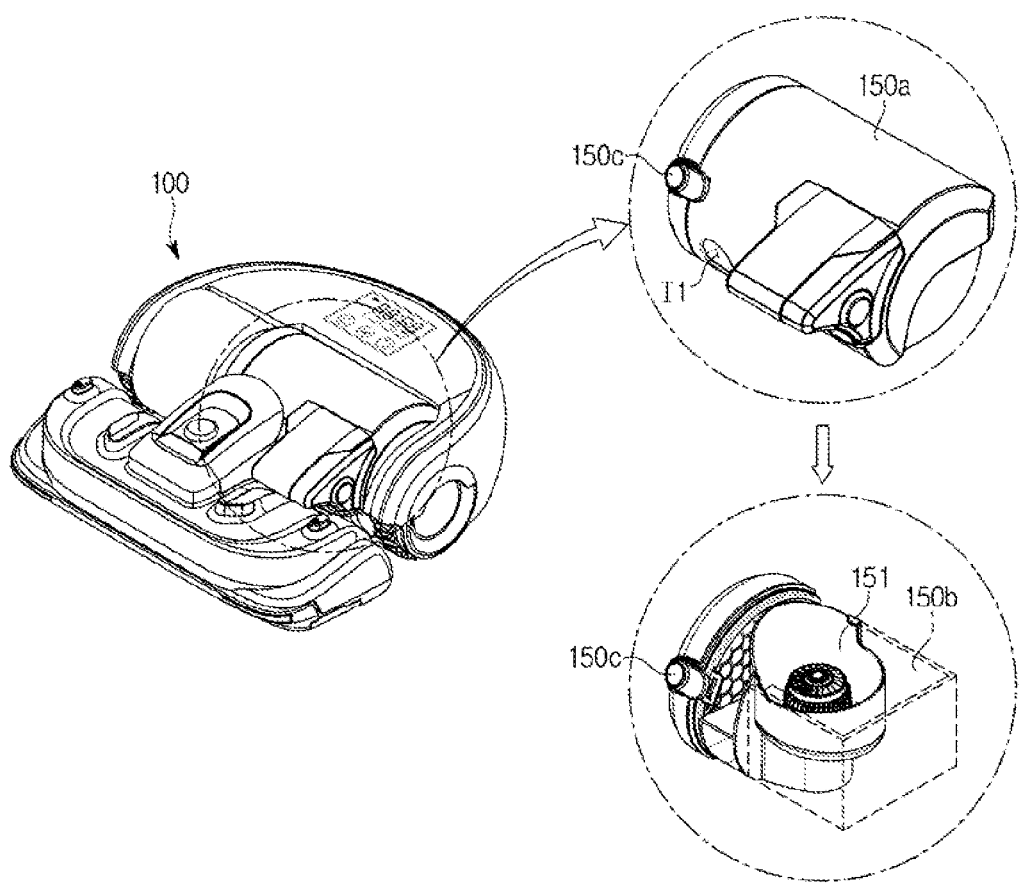
FIG. 5 is a view illustrating an example of the cleaning robot of FIG. 1.
Figure 6:
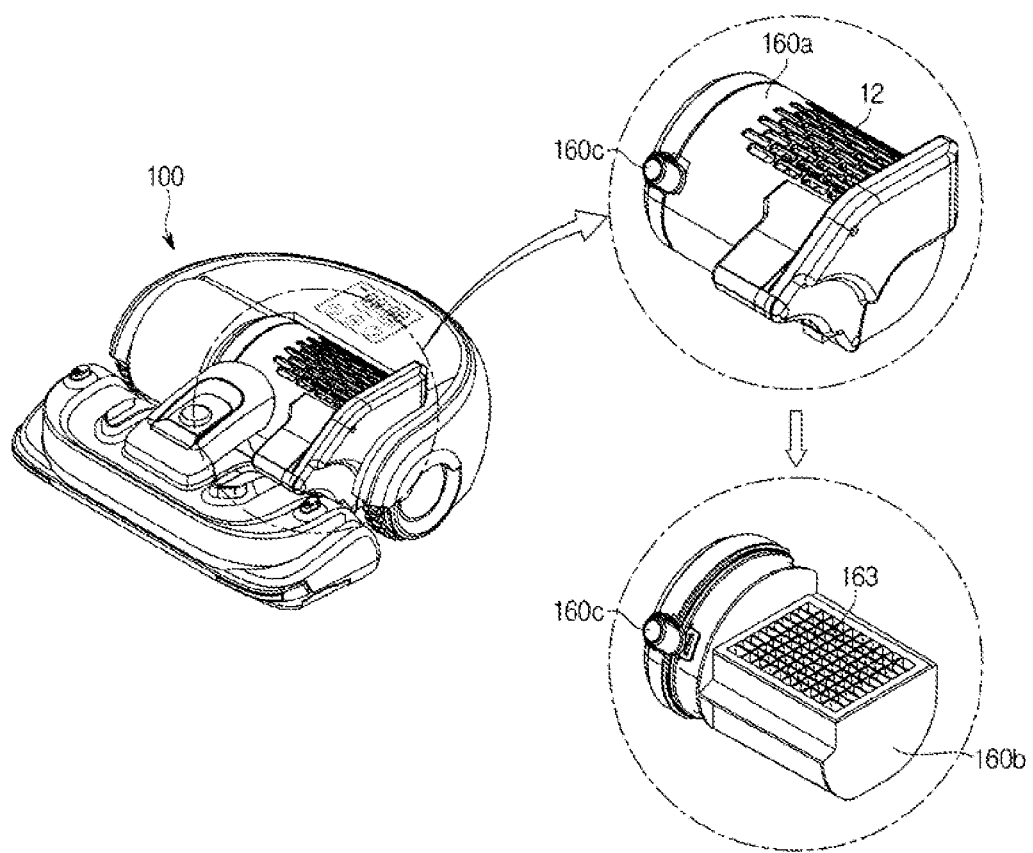
FIG. 6 is a view illustrating another example of the cleaning robot of FIG. 1.
Figure 7:
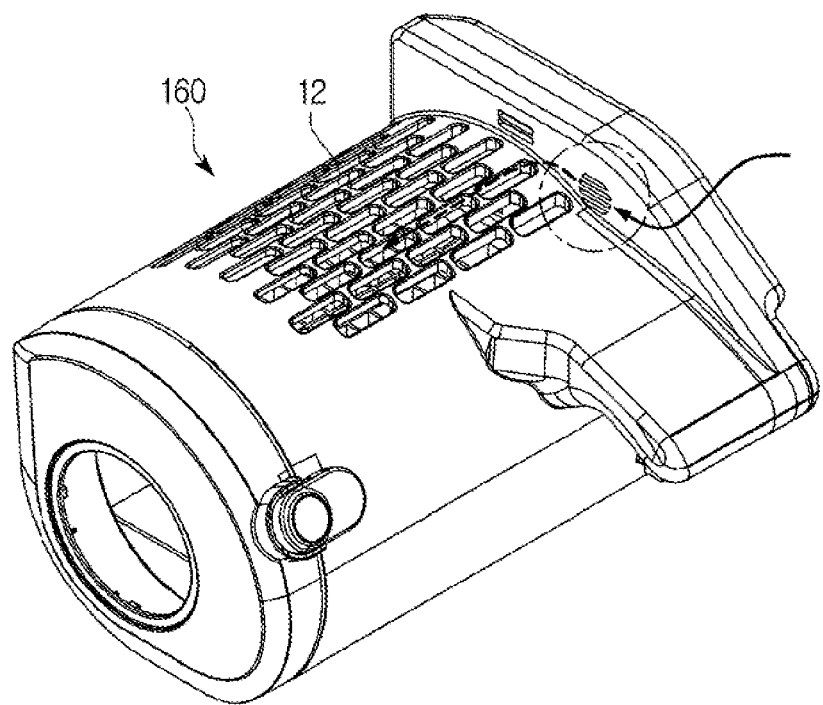
FIG. 7 is a view illustrating a sensor position of an air cleaning box.
Figure 16:
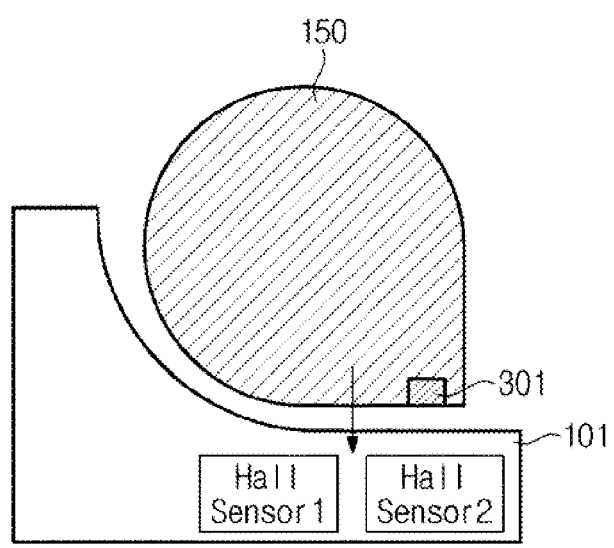
FIG. 16 is a view illustrating another example of the method of detecting the dust collecting box.
Figure 17:
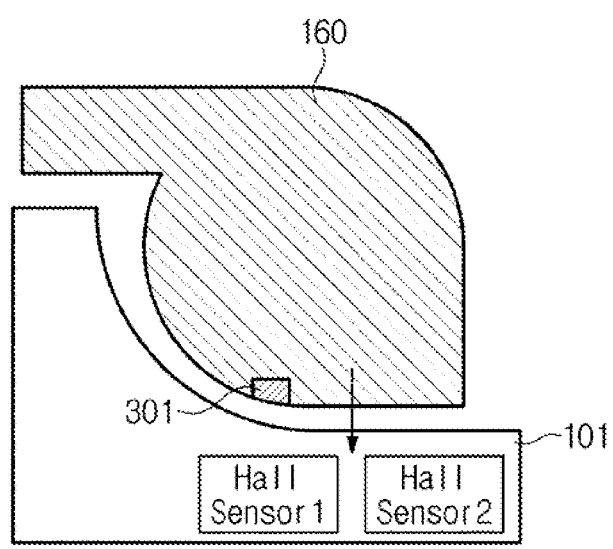
FIG. 17 is a view illustrating another example of the method of detecting the air cleaning box.
Figure 18:
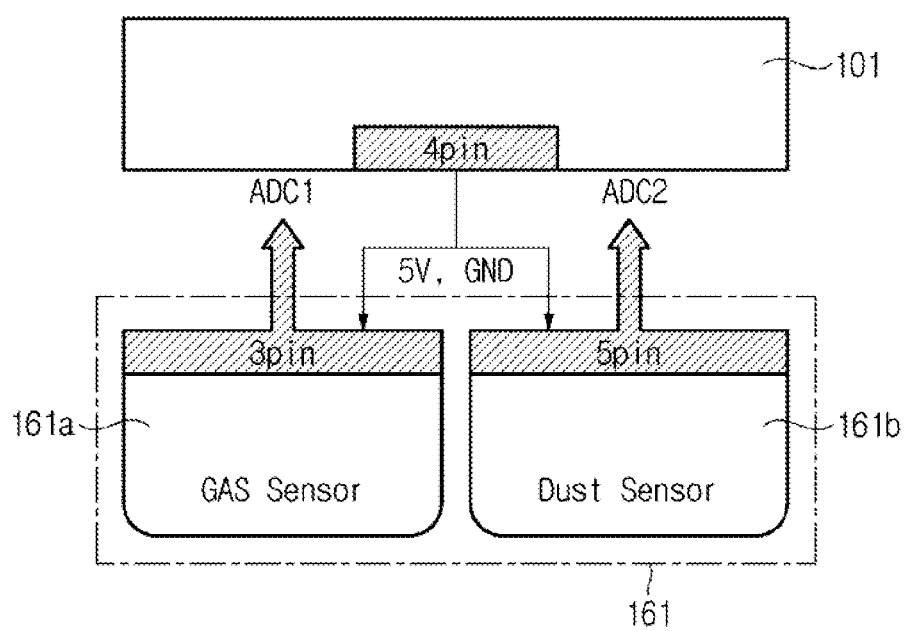
FIG. 18 is a view illustrating still another example of the method of detecting the dust collecting box and the air cleaning box.

Hereinafter, description will be provided with reference to FIGS. 5 and 6 illustrating examples of the cleaning robot 100, and FIG. 7 illustrating a sensor position. Also, further description will be provided with reference to FIGS. 16 through 18 illustrating a method of detecting the dust collecting box and an air cleaning box.

As shown in FIG. 3, the cleaning robot 100 may include an input unit 110, a display unit 120, an audio output unit 130, a storage unit 140, a dust collecting box 150, an air cleaning box 160, a driving unit 170 and a control unit 190.

The input unit 110 may receive control information related to the cleaning robot 100 and may also receive inputs from a user. At this time, the input unit 110 is in the exterior of the cleaning robot 100 to receive the control information generated through a push switch or membrane switch, or a touch switch, which generates an input signal through touching by a part of a user's body, of each input button 110a, 110b, 110c (FIG. 1) which generates the input signal through pressing of the user.

The display unit 120 may display information related to various operations of the cleaning robot 100. For example, the display unit 120 may display an operation state of the cleaning robot 100, a power state, a cleaning mode or an air cleaning mode, whether to return to a charging station, and so on.

The audio output unit 130 may output information related to various operations of the cleaning robot 100 in the form of an audible sound.

For example, the audio output unit 130 may output voice guidance such as "it has been switched to the cleaning mode", "it has been switched to the air cleaning mode", "it will return to the charging station", and "higher air pollution than the reference value persists in this area".

The storage unit 140 stores information related to the cleaning robot 100. For example, the storage unit 140 may store cleaning robot driving control information in the cleaning or dust collecting mode or the air cleaning mode, a contaminated area map and the like.

The dust collecting box 150 may be coupled to or separated from the body 101, 103 (FIG. 1), and may be a structure for collecting the dust introduced through the dust suction port 105 (FIG. 2).

As illustrated in FIG. 3, the dust collecting box 150 may include the cyclone 151 within the dust collecting box 150 to separate the dust from the air introduced through the dust suction port 105 (FIG. 2), and to transfer them to a filter 153, and the filter 153 to filter the dust among the dust and the air separated by the cyclone 151 and allows only the air to be discharged from the cleaning robot 100.

For example, as illustrated in FIG. 5, the dust collecting box 150 may be installed at the main body 101.

Referring to FIG. 5, the dust collecting box 150 may include a first dust collecting box 150a which forms an exterior, and a second dust collecting box 150b to be inserted into the first dust collecting box 150a. The second dust collecting box 150b may include the cyclone 151 and the filter 153.

The first and second dust collecting boxes 150a and 150b may be fixed to the dust collecting box 150 through a fastening part 150c, but a fastening method thereof is not limited thereto.

The air cleaning box 160 may replace or substitute the dust collecting box 150, and may be installed at the body 101, 103 to purify and discharge the air introduced into the body 101, 103.

As illustrated in FIG. 3, the air cleaning box 160 may include a contamination detecting sensor 161 located at a passage through which the air is collected or discharged from the body to detect a contamination level of the collected air, and a filter 163 to filter the dust and odor particles from the air collected into the body 101, 103, but the present invention is not limited thereto.

For example, the air cleaning box 160 may include only the filter 163, or may include both of the contamination detecting sensor 161 and the filter 163. At this time, when only the filter 163 is located in the air cleaning box 160, a connector for transmitting and receiving a signal between the air cleaning box 160 and the body 101 may be optional. Also, when only the filter 163 is located in the air cleaning box 160, the contamination detecting sensor 161 may be separately provided in the body 101. The contamination detecting sensor 161 may include a dust sensor and a gas sensor.

Also, as illustrated in FIG. 6, the exterior structure and the size of the air cleaning box 160 may be the same as those of the dust collecting box 150. As such, and the air cleaning box 160 may replace the dust collecting box and be installed in the main body 101 in the same manner as that of the dust collecting box 150. Thus, the cleaning robot 100 may operate in either the cleaning or dust collecting mode, or the air cleaning mode, depending on whether the dust collecting box 150 or the air cleaning box 160 has been installed in the body 101.

Referring to FIG. 6, the air cleaning box 160 may include a first air cleaning box 160a which forms an exterior of the air cleaning box 160, and a second air cleaning box 160b to be inserted into the first air cleaning box 160a. The first air cleaning box 160a may have a plurality of orifices or holes 12 to collect air from around the cleaning robot 100, and the orifices or holes 12 may be formed at an upper surface of the main body 101. At this time, a position of the orifices or holes 12 is not limited to the upper surface of the main body 101, and the orifices or holes 12 may be formed at another position which may easily collect the air.

Also, in the second air cleaning box 160b, the filter 163 may be located at a position facing the orifices or holes 12 formed at the first air cleaning box 160a, and may filter the odor particles and the dust from the collected air.

Also, the first and second air cleaning boxes 160a and 160b may be fixed to the air cleaning box 160 through a fastening part 160c, but a fastening method thereof is not limited thereto.

Referring to FIG. 7, the contamination detecting sensor 161 (FIG. 3) may be disposed at a side surface of the air cleaning box 160, to be located in or adjacent to a suction passage and thus to precisely detect the contamination of the collected air. At this time, a position of the contamination sensor 161 is not limited to the air cleaning box 160, and the contamination sensor 161 may be located at another position in accordance with a user's needs.

Meanwhile, each of the dust collecting box 150 and the air cleaning box 160 may have a contact type connector for power supply or signal transmission provided at an area fastened to the body 101, and may be fastened to a connector of the body 101. At this time, the connector is not limited to the contact type connector, and a non-contact type connector may also be applied thereto.

When only the filter 163 is located in the air cleaning box 160, the connector for transmitting and receiving the signal between the air cleaning box 160 and the body 101 may be optional.

The driving unit 170 drives the body 101, 103 based on the control unit 190, and may include the traveling wheels 173 at either side of the bottom surface of the main body 101 to move the body 101, and the wheel driving motor 177 to generate a rotational force for rotating the traveling wheels 173.

The control unit 190 may recognize whether the dust collecting box 150 or the air cleaning box 160 has been removably received or installed in the body 101, and may control the cleaning robot 100 to enter the dust collecting mode in response to recognizing that the dust collecting box has been installed, or to enter the air cleaning mode in response to recognizing that the air cleaning box has been installed.

As illustrated in FIG. 4, the control unit 190 may include a box recognizing part 191, a functional change processing part 193, a driving control part 195, and a mapping part 197.

The box recognizing part 191 may recognize a replacement of the dust collecting box 150 by an air cleaning box 160, and vice versa, through replacement information directly input by the user, a switching method, a hole sensor method, a load applied to the suction motor, or output data of a sensor.

First, the box recognizing part 191 may recognize an installment of either the dust collecting box 150 or the air cleaning box 160 through installation information entered or input by a user. For example, after the dust collecting box 150 or the air cleaning box 160 has been installed in the cleaning robot 100, the user may enter or input that a replacement box has been installed using a remote controller (not shown) or a button of the body 101, 103.

Also, the box recognizing part 191 may recognize one of the dust collecting box 150 and the air cleaning box 160 through one or more switches, for example, a first switch SW1 for recognizing the air cleaning box 160, and a second switch SW2 for recognizing the dust collecting box 150 provided at the body 101, contacting a switch recognizing part 201.

Figure 14:
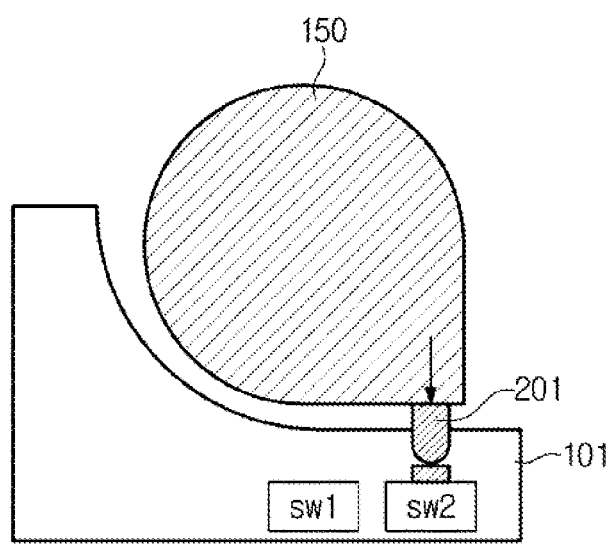
FIG. 14 is a view illustrating an example of a method of detecting a dust collecting box.
Figure 15:
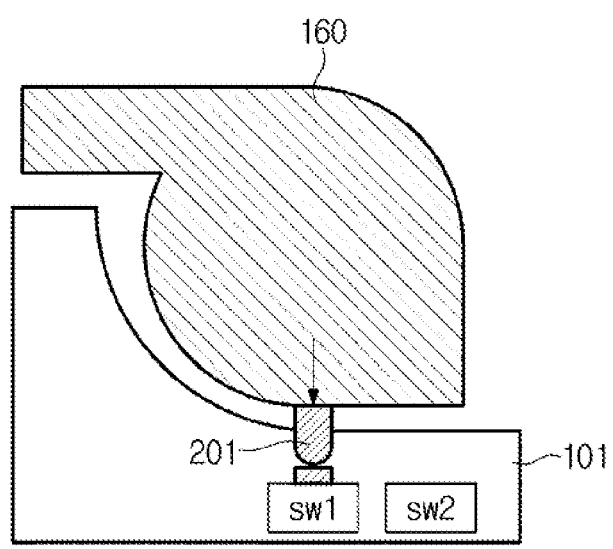
FIG. 15 is a view illustrating an example of a method of detecting an air cleaning box.

To this end, as illustrated in FIGS. 14 and 15, each of the dust collecting box 150 and the air cleaning box 160 may have a switch recognizing part 201 provided at a portion installed at the body 101 enabling the control unit 190 to recognize which of the dust collecting box and the air cleaning box has been installed. The switch recognizing part 201 may be disposed to be contacting one of the switches SW1 and SW2 located at a different position from each other.

Alternatively, when the switches SW1 and SW2 are provided at the dust collecting box 150 and the air cleaning box 160, respectively, the switch recognizing part 201 may be provided at the body 101.

Also, the box recognizing part 191 may recognize one of the dust collecting box 150 and the air cleaning box 160 through one or more sensors, for example, a first hole sensor Hall Sensor 1 for recognizing the air cleaning box 160 and a second hole sensor Hall Sensor 2 for recognizing the dust collecting box 150, through a magnet.

To this end, as illustrated in FIGS. 16 and 17, each of the dust collecting box 150 and the air cleaning box 160 may have a magnet 301 located at different portions of the respective dust collecting box 150 and air cleaning box 160 enabling the control unit 190 to recognize which of the dust collecting box and the air cleaning box has been installed.

The above-described method using the Hall sensor may enable the control unit 190 to recognize which of the dust collecting box and the air cleaning box has been installed through an electromagnetic induction method without physical contact or pressing.

In other embodiments, although not shown, the box recognizing part 191 may recognize one of the dust collecting box 150 and the air cleaning box 160 by detecting a load applied to the suction motor (not shown).

For example, since an oil pressure is different in each state in which the dust collecting box 150 is installed at the body 101, in which the air cleaning box 160 is installed at the body 101, and in which no dust collecting box or air cleaning box is installed at the body 101, the load applied to the suction motor (not shown) may also be different. As such, the control unit 190 may be able to identify or determine a type of an installed box and/or whether a box is installed according to the detected load.

Also, the box recognizing part 191 may recognize whether one of the dust collecting box 150 and the air cleaning box 160 has been installed according to whether an output data signal of the contamination detecting sensor 161 located in the air cleaning box 160 is recognized.

For example, when the contamination detecting sensor 161 is installed in the air cleaning box 160, the box recognizing part 191 may identify that one of the dust collecting box 150 and the air cleaning box 160 has been installed based on a state of the output data signal of the contamination detecting sensor 161, or whether the output data signal is recognized.

As illustrated in FIG. 18, the contamination detecting sensor 161 includes a gas sensor 161a and a dust sensor 161b. Outputs of the gas sensor 161a and the dust sensor 161b are applied as inputs to an ADC 1 and an ADC 2 of a CPU of the body 101, respectively. Thus the box recognizing part 191 monitors the data output signals from the contamination detecting sensor 161. That is, when the output data signal transmitted from the contamination detecting sensor 161 is recognized, the box recognizing part 191 determines that the air cleaning box 160 has been installed, and when the output data signal transferred from the contamination detecting sensor 161 is not recognized, the box recognizing part 191 determines that the dust collecting box 150 is installed. Referring to FIG. 18, the contamination detecting sensor 16 is provided with a 3Pin and a 5Pin for recognizing the gas sensor 161a and the dust sensor 161b, and when the contamination detecting sensor 161 is connected to the main body 101, data is transmitted from the contamination detecting sensor 161 to the main body 101 through ADC1 and ADC2 via the 3Pin and 5Pin. Meanwhile, the dust collecting box 150 is not provided with a separate pin to transmit data to the main body 101. After an air cleaning box 160 or the dust collecting box 150 is mounted, the box recognizing part 191 recognizes the air cleaning box 160 upon detecting an input data, and recognizes the dust collecting box 150 upon detecting no input data.

After one of the dust collecting box 150 and the air cleaning box 160 has been recognized by the box recognizing part 191, the functional change processing part 193 (of FIG. 4) may automatically switch an operation mode into the cleaning or dust collecting mode, or the air cleaning mode, or may switch the operation mode into the cleaning or dust collecting mode, or the air cleaning mode according to a user's choice.

At this time, the functional change processing part 193 may display a switch to the cleaning mode or the air cleaning mode in the form of characters through the display unit 120, or may output the switching in the form of an audio sound through the audio output unit 130.

Also, the user may directly perform the mode switching using a remote controller (not shown) or a button of the body 101.

The driving control part 195 controls a driving of the cleaning robot 100, and may control the driving in a corresponding mode according to a mode recognized by the functional change processing part 193.

The driving control part 195 will be described later in detail.

Figure 8:
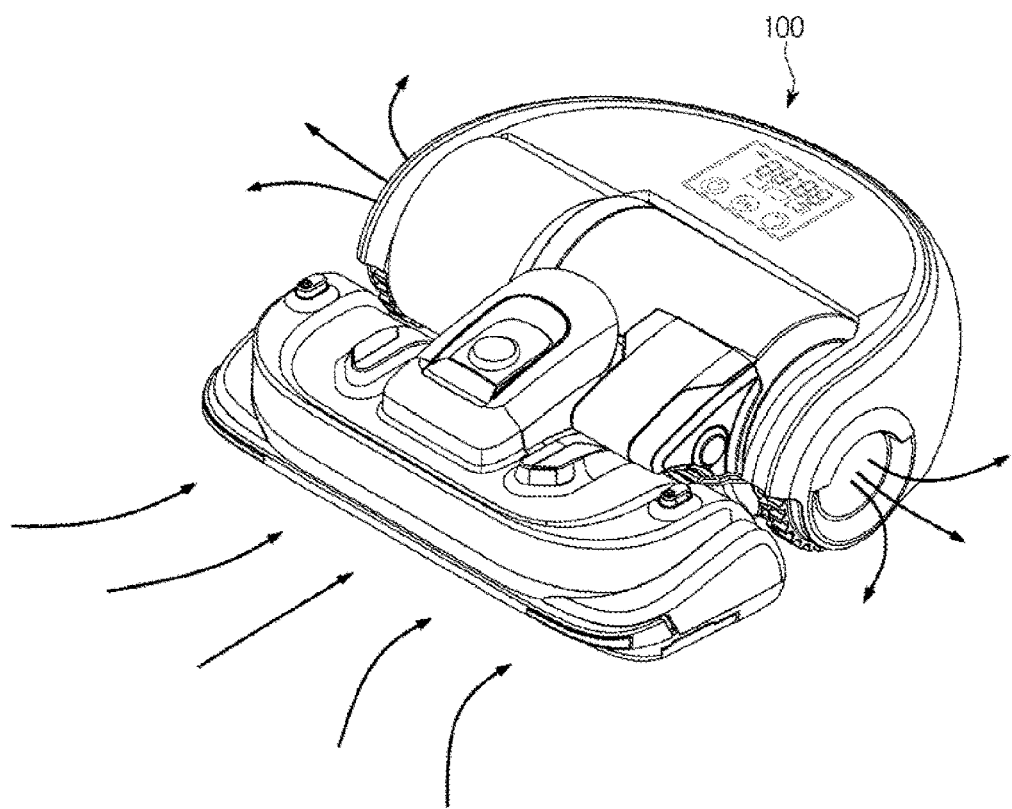
FIGS. 8 through 10 are views illustrating a dust suction method in a cleaning mode of the cleaning robot of FIG. 1 according to one example.
Figure 9:
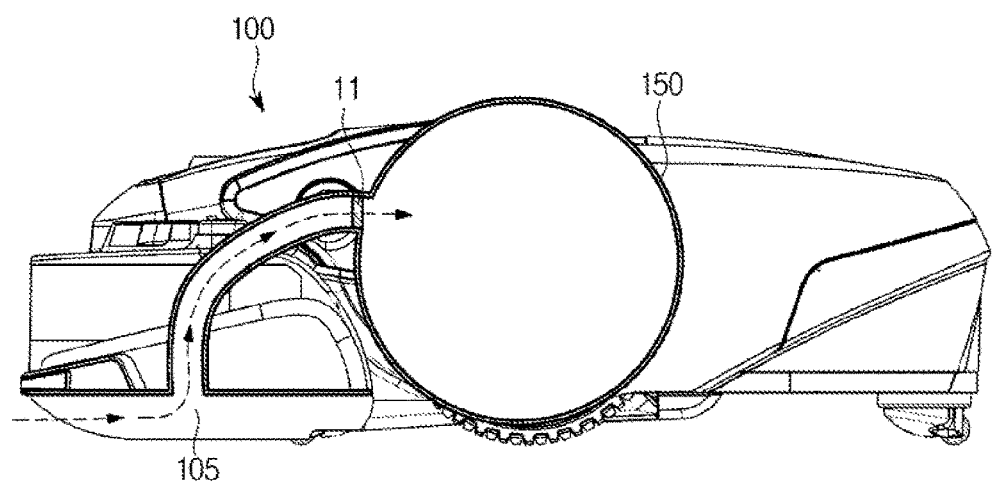
Figure 10:
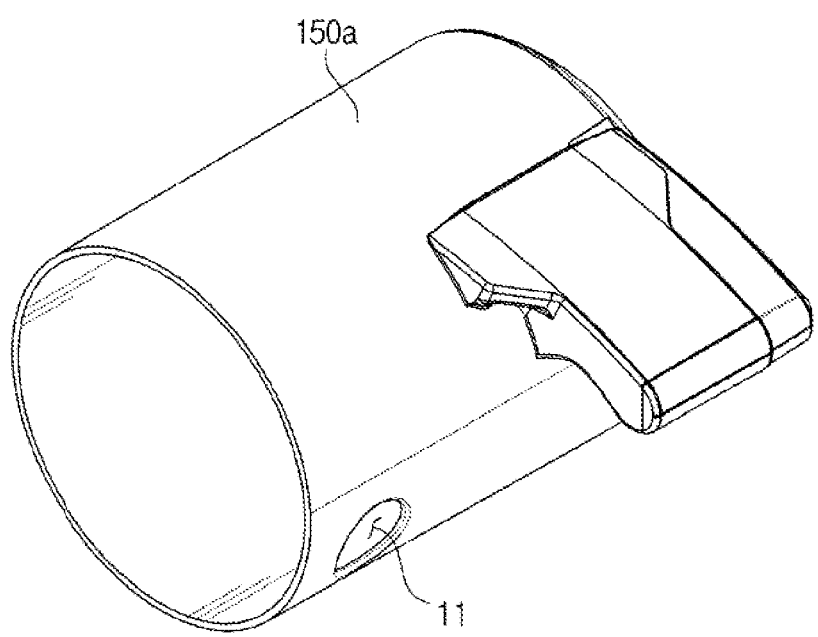

FIGS. 8 to 10 illustrate a dust suction method in the cleaning or dust collecting mode of the cleaning robot 100 according to one embodiment.

As illustrated in FIGS. 8 to 10, the cleaning robot 100 may filter the dust from the dust contained in the air introduced through the dust suction port 105 and collected in the dust collecting box 150 through the passage, and then may discharge the air to the outside.

To this end, the dust collecting box 150 may have a dust introduction hole 11 formed at a position connected with the passage through which the dust collected through the dust suction port 105 is transferred. The dust introduction hole 11 may be formed at the first dust collecting box 150*a*.

Figure 11:
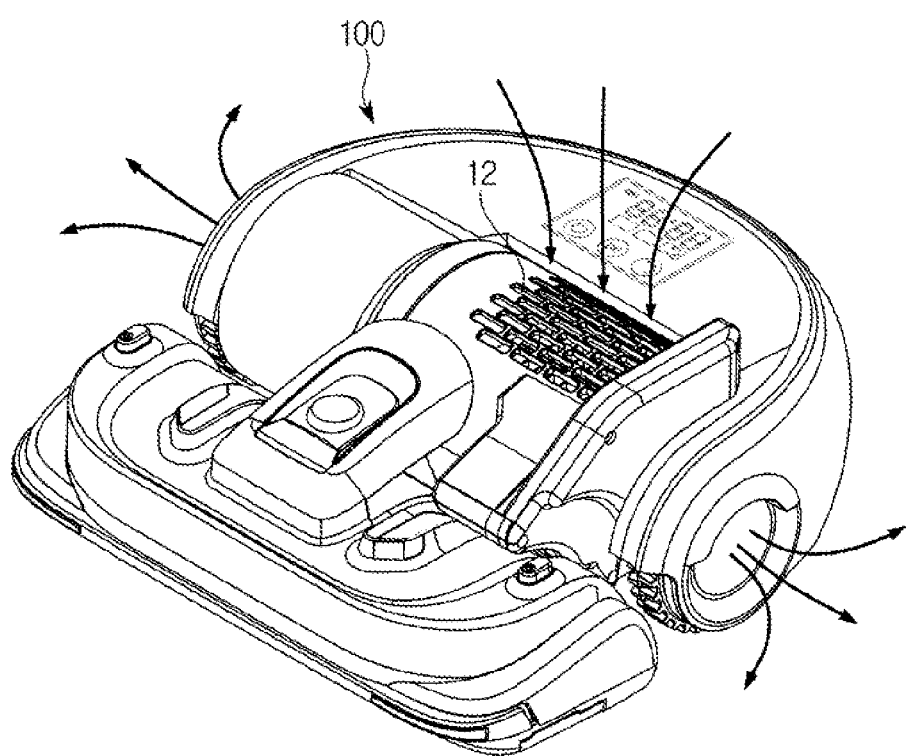
FIGS. 11 through 13 are views illustrating a dust suction method in an air cleaning mode of the cleaning robot of FIG. 1 according to another example.
Figure 12:
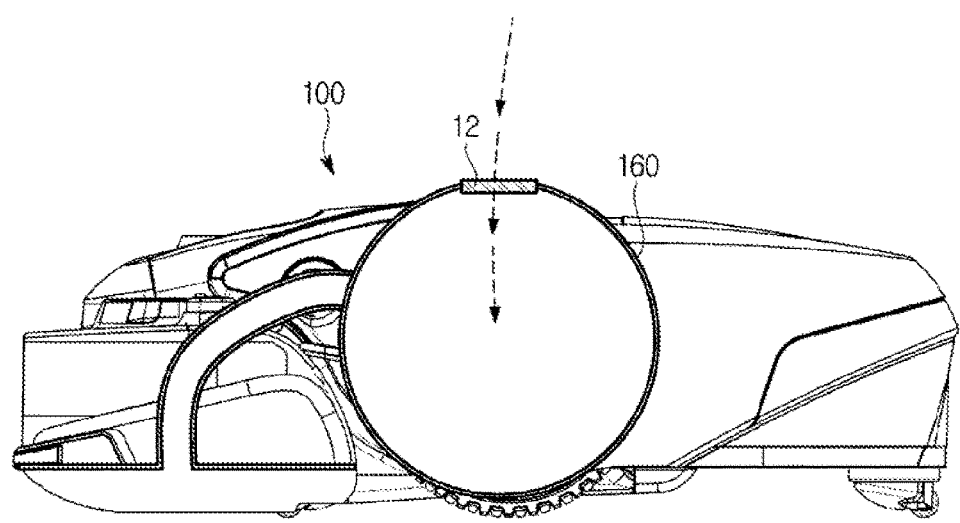
Figure 13:
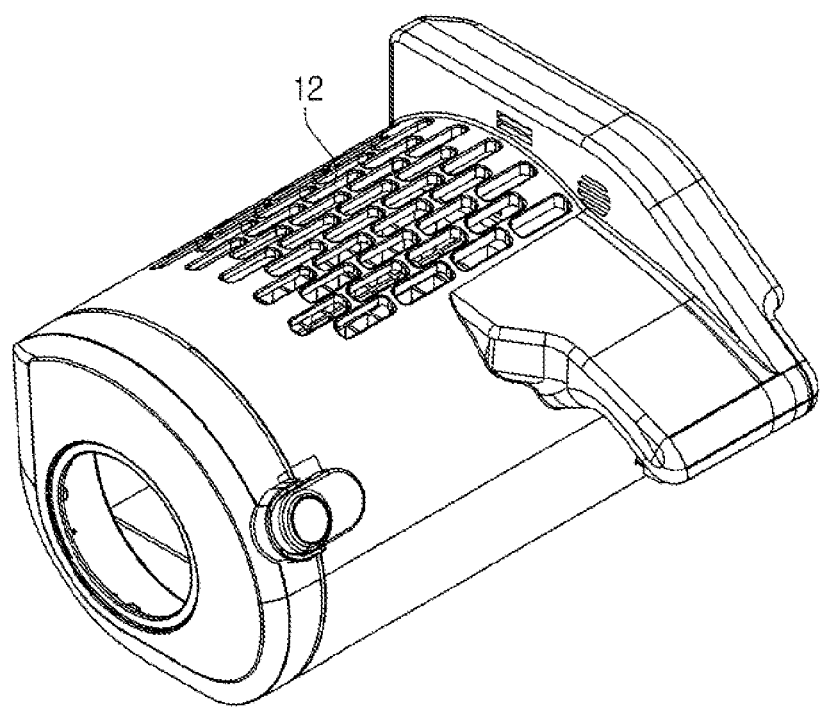

FIGS. 11 to 13 illustrate a dust suction method in the air cleaning mode of the cleaning robot according to another embodiment.

As illustrated in FIGS. 11 and 12, the cleaning robot 100 may introduce the air from the atmosphere surrounding the body 101, may filter the dust and the odor particles, and then may discharge the cleaned air from the cleaning robot 100.

As illustrated in FIG. 13, the air cleaning box 160 may have a plurality of holes 12 which introduce the air. The plurality of holes 12 may be formed at the first air cleaning box 160*a*.

As illustrated in FIGS. 12 and 13, the air cleaning box 160 has a structure in which a passage for transferring the dust through the dust suction port 105 is blocked, because a hole is not formed at a position at which the dust introduction hole 11 of the dust collecting box 150 is formed. Therefore, the load applied to the suction motor (not shown) may be different from that in a case in which the dust collecting box 150 is installed at the cleaning robot 100. Using such a principle, the control unit 190 may distinguish the dust collecting box 150 from the air cleaning box 160 based on the load applied to the suction motor.

FIGS. 19 to 24 are exemplary views illustrating a method of traveling the cleaning robot 100 in the air cleaning mode.

In the air cleaning mode, the driving control unit 195 may control the body 101 to be moved in a predetermined air cleanable area unit and to perform an air cleaning operation.

More specifically, air cleaning performance may be different according to a size of the filter 163 or an intensity of the suction motor (not shown). Therefore, in cleanings like dust collecting and deodorizing, a cleanable area which may be covered is set according to a product specification. Therefore, the driving control unit 195 controls the cleaning robot 100 to travel in the air cleanable area unit which may be covered based on the air cleaning performance.

Figure 19:
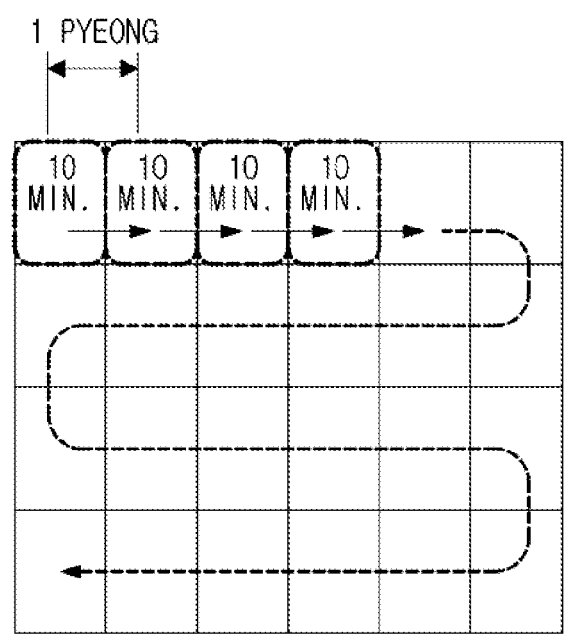
FIGS. 19 through 24 are exemplary views illustrating a method of traveling the cleaning robot of FIG. 1 in the air cleaning mode.

For example, as illustrated in FIG. 19, when an air cleanable area of the cleaning robot 100 is one pyeong (1 pyeong=3.31 m$^2$), the driving control unit 195 controls the cleaning robot 100 to be moved in a cleaning area by one pyeong and then stopped, and also controls driving of the suction motor to be maximally boosted up. Also, the driving control unit 195 controls the suction motor to be slightly driven, when the cleaning robot 100 is moving. At this time, a traveling pattern (e.g., stopping, low speed traveling, certain repeated traveling, spiral traveling, or the like) of the cleaning robot 100 may be changed by the user.

Also, in the case of the air cleaning mode, the driving control unit 195 may control the body 101 to perform an air cleaning operation based on position and time information set by the user.

Figure 20:
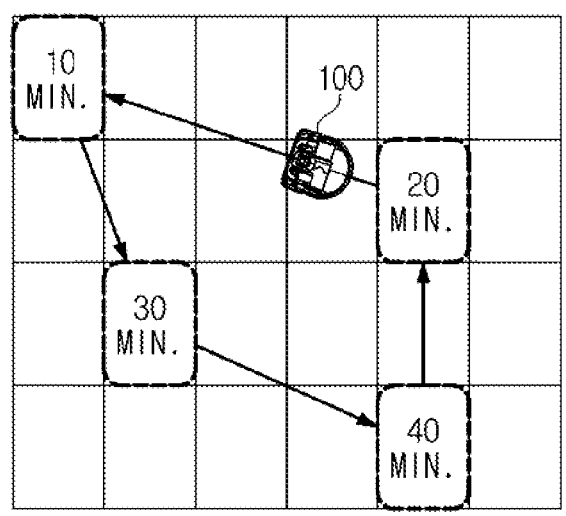

As illustrated in FIG. 20, when the cleaning robot 100 checks the cleaning area and recognizes a position of the cleaning robot 100, the driving control unit 195 may check a position set by the user, and may control the cleaning robot 100 to perform an air cleaning function for a period of time set by the user, while moving in only the corresponding position.

At this time, the traveling pattern (e.g., stopping, low speed traveling, certain repeated traveling, spiral traveling, or the like) of the cleaning robot 100 may be changed by the user.

Also, in the air cleaning mode, when a contamination level may be detected while the body 101 is traveling, the driving control unit 195 may control the body 101 to perform the air cleaning operation until the contamination level within the corresponding area becomes lower than or equal to a predetermined reference value.

Figure 21:
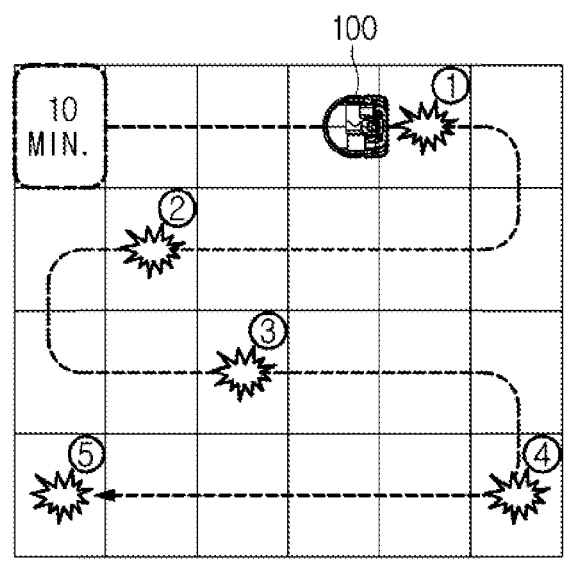

For example, as illustrated in FIG. 21, when a contamination level which is greater than or equal to the reference value is detected at areas ①, ②, ③, ④ and ⑤ while the cleaning robot 100 is traveling, the cleaning robot 100 continuously performs the air cleaning operation at the corresponding areas so that the contamination level becomes lower than the reference value. At this time, the driving control unit 195 may indicate the areas, at which the contamination level is higher than the reference value is detected, on a traveling area map through the mapping part 197 (of FIG. 4), and then may store an area of contamination map. The detected contamination result may be output in the form of a contamination detection announcement through the display unit 120 and the audio output unit 130, or may be directed to the user by transmitting a contamination detection map to a user's mobile communication terminal.

Also, the driving control unit 195 may control the body 101 to perform the air cleaning operation while moving in only the contaminated areas based on the stored area of contamination map.

Figure 22:
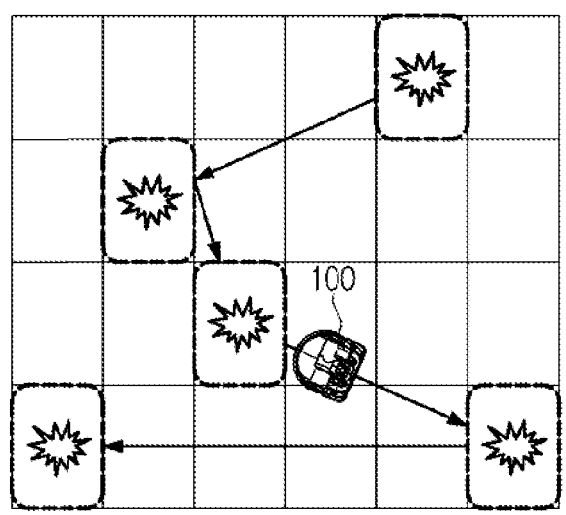

For example, as illustrated in FIG. 22, the cleaning robot 100 may repeatedly perform the air cleaning mode a predetermined times in the order set by the user or a predetermined order, while moving in only the contaminated areas in the area of contamination map according to control of the control unit 195. At this time, the cleaning robot 100 may communicate with the user's mobile communication terminal (not shown), and the traveling pattern in the area of contamination map may be set through a cleaning robot application installed at the user's mobile communication terminal.

Figure 23:
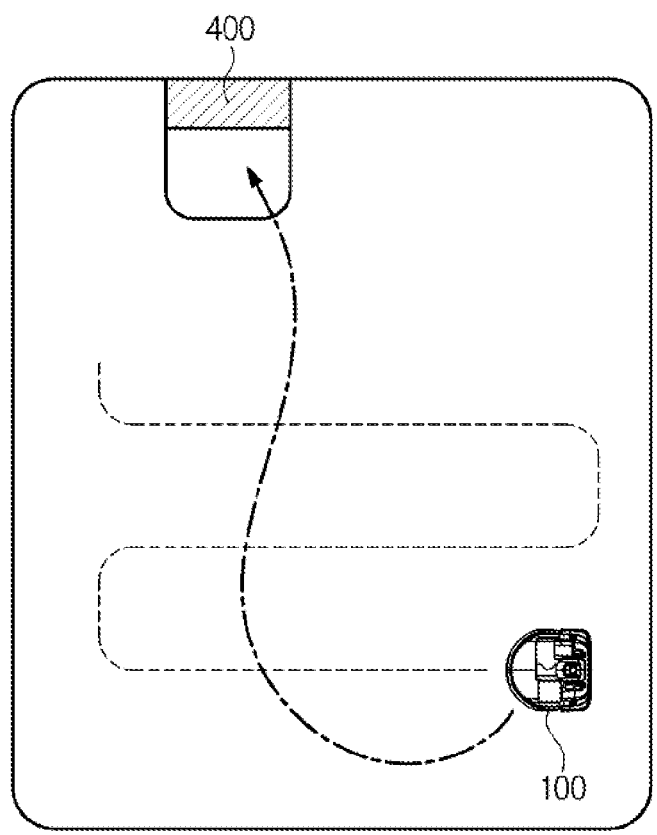
Figure 24:
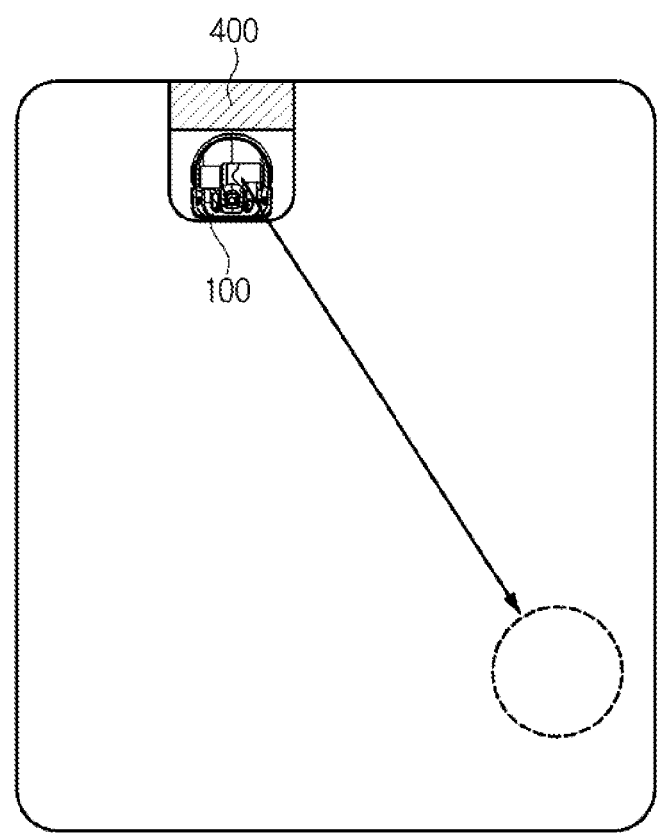

Also, as illustrated in FIGS. 23 and 24, when a battery residual value of the cleaning robot 100 is less than or equal to a reference value, or the air cleaning operation is completed, the driving control unit 195 may control the body 101 to return to a charging station 400.

Also, as illustrated in FIG. 24, the driving control unit 195 may control the cleaning robot 100 to perform the air cleaning operation, while being charged at the charging station 400.

The cleaning robot 100 may perform the air cleaning operation using pre-stored power, independently of the power stored through charging. This operation may be performed according to user settings. At this time, in the case of a normal charging mode, the driving control unit 195 may restrict the cleaning robot 100 to perform the air cleaning operation, and may control the cleaning robot 100 to perform the air cleaning operation for a predetermined period of time, only when the contamination is detected by the contamination detecting sensor 161. This is to rapidly and smoothly charge a battery of the cleaning robot 100.

Also, when a state in which the contamination level detected by the contamination detecting sensor 161 is higher than the reference value continues for a predetermined period of time or more, the driving control unit 195 may determine an error of the contamination detecting sensor 161, and may control the cleaning robot 100 to perform the air cleaning operation with a predetermined suction force.

Also, when the contamination level detected by the contamination detecting sensor 161 is higher than the reference value for more than a predetermined period of time, the driving control unit 195 may display an air contamination alarm of a corresponding area through the display unit 120, may output the air contamination alarm in the form of the sound source through the audio output unit 130, or may transfer the air contamination alarm to the user's mobile communication terminal through the wireless communication.

In the disclosed invention, the cleaning mode or the air cleaning mode can be operated with only a replacement between the dust collecting box for the cleaning function and the air cleaning box for the air cleaning function without replacing the suction motor.

That is, a high-efficiency capability of the cleaning robot can be used in various services from the cleaning operation to the air cleaning operation, thereby enhancing consumer satisfaction.

The present invention can provide not only the cleaning function but also the air cleaning function which can collect the fine dust and can perform deodorization using the capabilities of the cleaning robot.

Although a few embodiments of the present invention have been shown and described, it would be appreciated by those skilled in the art that changes may be made in these embodiments without departing from the principles and spirit of the invention, the scope of which is defined in the claims and their equivalents.

What is claimed is:

1. A cleaning robot comprising:
   a display configured to display information related to operations of the cleaning robot;
   a dust suction port;
   a main body configured to removably accommodate a dust collecting box or an air cleaning box, wherein the dust collecting box is separably coupled with the main body and configured to collect dust introduced through the dust suction port, and wherein the air cleaning box is configured to purify air introduced into the main body and discharge the purified air; and
   a controller configured to recognize which of the dust collecting box and the air cleaning box has been installed in the main body, and to control the cleaning robot to enter a dust collecting mode in response to recognizing that the dust collecting box has been installed, and to enter an air cleaning mode in response to recognizing that the air cleaning box has been installed,
   wherein the dust collecting box has a dust introduction hole connected with a passage which the dust introduced through the dust suction port is transferred, and
   wherein the air cleaning box has a plurality of holes which introduces the air from outside and blocks the passage which the dust introduced through the dust suction port is transferred.

2. The cleaning robot according to claim 1, wherein the air cleaning box comprises a filter configured to filter the dust and odor particles from the air introduced into the main body.

3. The cleaning robot according to claim 1, wherein the air cleaning box comprises a contamination detecting sensor located at the plurality of holes which the air is introduced into or discharged from the main body, to detect a contamination level of the air introduced into the main body.

4. The cleaning robot according to claim 1, wherein each of the dust collecting box and the air cleaning box has a contact type connector for at least one of a power supply and a signal transmission provided at an area coupled to the main body, and is coupled to the main body via the contact type connector.

5. The cleaning robot according to claim 1, wherein the controller recognizes a replacement of the dust collecting box or the air cleaning box through replacement information input by a user.

6. The cleaning robot according to claim 1, wherein each of the dust collecting box and the air cleaning box has a switch recognizing part enabling the controller to recognize which of the dust collecting box and the air cleaning box has been installed.

7. The cleaning robot according to claim 6, wherein the controller recognizes one of the dust collecting box and the air cleaning box through one of a first switch for recognizing the air cleaning box and a second switch for recognizing the dust collecting box provided at the main body, contacting with the switch recognizing part.

8. The cleaning robot according to claim 1, wherein the controller recognizes which of the dust collecting box and the air cleaning box has been installed, and automatically switches to one of the dust collecting mode and air cleaning mode.

9. The cleaning robot according to claim 1, wherein, in the air cleaning mode, the controller controls the main body to perform an air cleaning operation while moving in a predetermined air cleanable area unit.

10. The cleaning robot according to claim 1, wherein, in the air cleaning mode, the controller controls the main body to perform an air cleaning operation based on position and time information set by a user.

11. The cleaning robot according to claim 1, wherein, in the air cleaning mode, when contamination is detected while the main body is traveling, the controller controls the main body to perform an air cleaning operation until a contamination level within an area becomes lower than or equal to a predetermined reference value.

12. The cleaning robot according to claim 1, wherein the controller controls the main body to perform an air cleaning operation while moving in a contaminated area of a contamination map.

13. The cleaning robot according to claim 1, wherein the controller controls the main body to return to a charging station, when at least one of a battery residual value of the cleaning robot is less than or equal to a reference value, and an air cleaning operation is completed.

14. The cleaning robot according to claim 1, wherein the controller controls the cleaning robot to purify the air, while being charged at a charging station.

15. The cleaning robot according to claim 1, wherein, when a contamination level detected by a contamination detecting sensor is greater than or equal to a reference value for more than a predetermined period of time, the controller determines an error of the contamination detecting sensor, and controls the cleaning robot to perform an air cleaning operation with a predetermined suction force.

16. The cleaning robot according to claim 1, wherein, when a contamination level detected by a contamination detecting sensor is greater than or equal to a reference value for more than a predetermined period of time, the controller performs at least one of a display of an air contamination alarm of a corresponding area through the display, an output of the air contamination alarm as a sound source through an audio output unit, and a transfer of the air contamination alarm to a user's mobile communication terminal through wireless communication.

\* \* \* \* \*